(12) United States Patent
Naya

(10) Patent No.: US 6,208,422 B1
(45) Date of Patent: Mar. 27, 2001

(54) SURFACE PLASMON SENSOR

(75) Inventor: Masayuki Naya, Kanagawa-ken (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 0 days.

(21) Appl. No.: 09/301,126

(22) Filed: Apr. 28, 1999

(30) Foreign Application Priority Data

Apr. 28, 1998 (JP) .................................................. 10-118658
Jan. 29, 1999 (JP) .................................................. 11-021003

(51) Int. Cl.[7] .................................................. G01N 21/55
(52) U.S. Cl. .......................... 356/445; 373/372; 373/375
(58) Field of Search .................................. 356/445, 373, 356/375, 372

(56) References Cited

U.S. PATENT DOCUMENTS

| | | | |
|---|---|---|---|
| 5,075,551 | 12/1991 | Watanabe | 250/341 |
| 5,239,183 | 8/1993 | Kouno et al. | 250/561 |
| 5,633,492 | 5/1997 | Nikitin et al. | |
| 5,917,607 | * 6/1999 | Naya | 356/445 |
| 5,917,608 | * 6/1999 | Naya et al. | 356/445 |

FOREIGN PATENT DOCUMENTS

| | | | |
|---|---|---|---|
| 0 019 724 A1 | 12/1980 | (EP) | G01N/21/86 |
| 0 426 571 A1 | 5/1991 | (EP) | G02B/21/00 |
| 6-167443 | 6/1994 | (JP) | G01N/21/27 |

* cited by examiner

Primary Examiner—Frank G. Font
Assistant Examiner—Reginald A. Ratliff
(74) Attorney, Agent, or Firm—Sughrue, Mion, Zinn, Macpeak & Seas, PLLC

(57) ABSTRACT

A surface plasmon sensor includes a dielectric block, a metal film having a sample supporting side which is faced toward a face of the dielectric block spaced therefrom and on which a sample is placed, a light source emitting a light beam, an optical system which causes the light beam to enter the dielectric block so that the light beam is reflected in total reflection at the face of the dielectric block and various angles of incidence of the light beam to the face of the dielectric block including an angle of incidence at which surface plasmon is generated can be obtained, and a sensor which detects the angle of incidence of the light beam at which attenuation in total reflection takes place and the amount of reflected light is reduced. A distance measuring light beam is caused to enter the dielectric block to be reflected in total reflection at the face of the dielectric block. A driver moves the dielectric block and the metal film relatively to each other so that the distance between the face of the dielectric block and the sample support side of the metal film changes. A photodetector measures the amount of distance measuring light beam reflected in total reflection at the face of the dielectric block. The driver is controlled to move the dielectric block and the metal film so that the amount of reflected distance measuring light beam as detected by the photodetector is kept constant.

3 Claims, 3 Drawing Sheets

SURFACE PLASMON SENSOR

BACKGROUND OF THE INVENTION

1. Field of the Invention

This invention relates to a surface plasmon sensor for quantitatively analyzing a material in a sample utilizing generation of surface plasmon, and more particularly to an Otto type surface plasmon sensor.

2. Description of the Related Art

In metal, free electrons vibrate in a group to generate compression waves called plasma waves. The compression waves generated in a metal surface are quantized into surface plasmon.

There have been proposed various surface plasmon sensors for quantitatively analyzing a material in a sample utilizing a phenomenon that such surface plasmon is excited by light waves. Among those, one employing a system called "Kretschmann configuration" is best known. See, for instance, Japanese Unexamined Patent Publication No. 6(1994)-167443.

Further there has been known also a surface plasmon sensor generally referred to as "an Otto type surface plasmon sensor". The Otto type plasmon sensor basically comprises a dielectric block shaped, for instance, like a prism, a metal film having a sample supporting side which is faced toward one face of the dielectric block spaced therefrom and on which a sample is placed, a light source emitting a light beam, an optical system which causes the light beam to enter the dielectric block so that the light beam is reflected in total reflection at said one face of the dielectric block and various angles of incidence of the light beam to said one face of the dielectric block including an angle of incidence at which surface plasmon is generated can be obtained, and a detecting means which detects the angle of incidence of the light beam at which attenuation in total reflection takes place and the amount of reflected light is reduced.

In order to obtain various angles of incidence of the light beam to the interface, a relatively thin light beam may be caused to impinge upon said one face of the dielectric block while deflecting the light beam or a relatively thick light beam may be caused to converge on said one face of the dielectric block so that components of the light beam impinge upon the interface at various angles. In the former case, the light beam which is reflected from the face at an angle which varies as the light beam is deflected may be detected by a photodetector which is moved in synchronization with deflection of the light beam or by an area sensor extending in the direction in which reflected light beam is moved as a result of deflection. In the latter case, an area sensor which extends in directions so that all the components of light reflected from the interface at various angles can be detected by the area sensor may be used.

In such an Otto type plasmon sensor, when a sample is fixed on the sample support side of the metal film having a sufficient thickness and a light beam is caused to impinge upon said one face of the dielectric block opposed to the sample support side of the metal film at a particular angle of incidence θsp not smaller than the angle of total internal reflection, evanescent waves having an electric field distribution are generated in the sample and the metal film, and surface plasmon is excited in the metal film. When the wave vector of the evanescent waves is equal to the wave number of the surface plasmon and wave number matching is established, the evanescent waves and the surface plasmon resonate and light energy is transferred to the surface plasmon, whereby the intensity of light reflected in total reflection from the interface of the dielectric block and the metal film sharply drops.

When the wave number of the surface plasmon can be known from the angle of incidence θsp at which the phenomenon of attenuation in total reflection takes place, the dielectric constant of the sample can be obtained. When the dielectric constant of the sample is known, the concentration of a specific material in the sample can be determined on the basis of a predetermined calibration curve or the like. Accordingly, a specific component in the sample can be quantitatively analyzed by detecting the angle of incidence θsp at which the intensity of light reflected in total reflection from the face of the dielectric block sharply drops.

Though being advantageous in that measurement is easy, Kretschmann type surface plasmon sensor is disadvantageous in that it is necessary to precisely control the thickness of the metal film and the photo-coupler for causing total reflection must be in refractive index matching with the sensor.

To the contrary, in the Otto type surface plasmon sensor, the aforesaid resonance is caused constantly under the same condition so long as the thickness of the metal film is sufficient and measurement can be effected without contact with the sample.

However, in order to effect accurate measurement by use of the Otto type surface plasmon sensor, it is necessary to keep constant the distance between said one face of the dielectric block and the sample support side of the metal film within the range by which the evanescent waves ooze from the face of the dieletric block, which makes the measurement very difficult.

SUMMARY OF THE INVENTION

In view of the foregoing observations and description, the primary object of the present invention is to provide an Otto type surface plasmon sensor in which the distance between said one face of the dielectric block and the sample support of the metal film can be kept constant and a sufficiently high accuracy of measurement can be realized.

The Otto type surface plasmon sensor of the present invention comprises a dielectric block, a metal film, a light source emitting a light beam, an optical system, and a detecting means for detecting the angle of incidence of the light beam at which attenuation in total reflection takes place and the amount of reflected light is reduced which are described above and is characterized by having a distance measuring light source which causes a distance measuring light beam, at a wavelength which can be absorbed by the metal film, to enter the dielectric block so that the distance measuring light beam is reflected in total reflection at said one face of the dielectric block, a drive means which moves the dielectric block and the metal film relatively to each other so that the distance between said one face of the dielectric block and the sample support side of the metal film changes, a photodetector which measures the amount of distance measuring light beam reflected in total reflection at said one face of the dielectric block, and a control means which controls the drive means to move the dielectric block and the metal film so that the amount of reflected distance measuring light beam as detected by the photodetector is kept constant.

In the surface plasmon sensor of the present invention with the arrangement described above, evanescent waves ooze out from said one face of the dielectric block when the distance measuring light beam impinges upon said one face of the dielectric block so as to be reflected in total reflection at the face. When the distance between the face of the dielectric block and the sample support side of the metal film is within the distance which the evanescent waves can reach, the evanescent waves are absorbed by the metal film.

Accordingly the amount of distance measuring light beam reflected at the face of the dielectric block is reduced. The reduction in the amount of distance measuring light beam reflected at the face of the dielectric block solely depends upon the distance between the face of the dielectric block and the sample support side of the metal film. Accordingly, by controlling the drive means to move the dielectric block and the metal film so that the amount of reflected distance measuring light beam as detected by the photodetector is kept constant, the distance between the face of the dielectric block and the sample support side of the metal film can be kept constant, whereby accuracy of measurement can be ensured.

DESCRIPTION OF THE PREFERRED EMBODIMENTS

Figure 1:
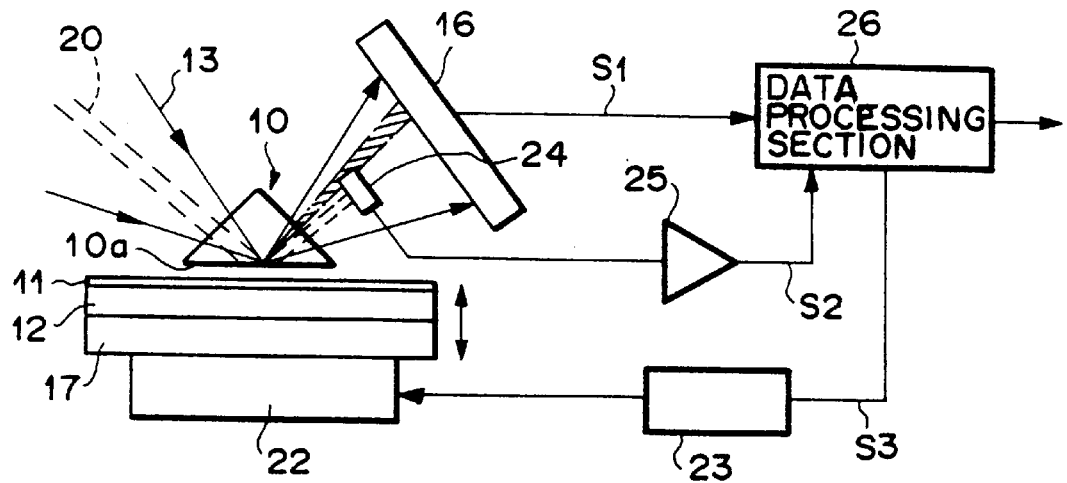
FIG. 1 is a side view of a surface plasmon sensor in accordance with a first embodiment of the present invention.
Figure 2:
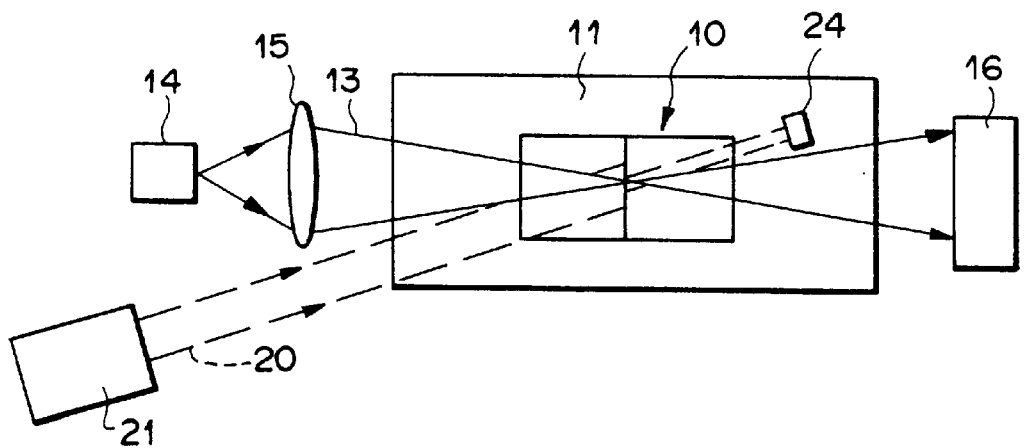
FIG. 2 is a plan view of the surface plasmon sensor with the transverse dimension enlarged.

In FIGS. 1 and 2, an Otto type surface plasmon sensor in accordance with a first embodiment of the present invention comprises a triangular prism 10 formed of glass (dielectric material), a metal (gold in this particular embodiment) film 12 which is disposed spaced from one face 10a of the prism 10 with its sample support side (the upper side in this particular embodiment) for supporting thereon a sample 11 facing the face 10a, a semiconductor laser 14 emitting a single light beam (laser beam) 13, an optical system 15 (a single lens in this particular embodiment) which causes the light beam 13 to enter the prism 10 so that various angles of incidence of the light beam 13 to the face 10a of the prism 10 can be obtained, and a photodetector (a line sensor) 16 which detects the amount of the light beam 13 reflected in total reflection at the face 10a.

The metal film 12 is formed on a support 17 in a sufficient thickness. The semiconductor laser 14 is a laser such as a near infrared semiconductor laser which emits a laser beam of a wavelength (e.g., 633 nm) which is not absorbed by the metal (gold) film 12. The semiconductor laser 14 is disposed so that the light beam 13 impinges upon the face 10a of the prism 10 in a P-polarized state.

The surface plasmon sensor of this embodiment is further provided with a distance measuring light source 21 which causes a relatively thin distance measuring light beam 20 to enter the prism 10 so that the distance measuring light beam 20 is reflected in total reflection at the face 10a of the prism 10, a piezo-electric element 22 which moves the support 17 in a direction where the distance between the face 10a of the prism 10 and the metal film 12 changes, a driver 23 which drives the piezoelectric element 22, a photodetector 24 which measures the amount of distance measuring light beam 20 reflected in total reflection at the face 10a of the prism 10, and an amplifier 25 which amplifies a light amount signal as output from the photodetector 24 and inputs an amplified light amount signal S2 into a data processing section 26.

As the distance measuring light source 21, is employed one which emits a light beam at a wavelength (e.g., 488 nm, 473 nm, 515 nm or the like) which can be absorbed by the gold film 12. The distance measuring light source 21 is disposed so that the distance measuring light beam 20 impinges upon the face 10a of the prism 10 in a S-polarized state. A light amount signal S1 output from the photodetector 16 is also input into the data processing section 26.

Since the light beam 13 is converged on the face 10a by the lens 15, the light beam 13 impinging upon the face 10a contains components which impinge upon the face 10a at various angles θ. The angle of incidence θ is made not smaller than an angle of total internal reflection. The light beam 13 is reflected in total reflection at the face 10a and accordingly the reflected light beam 13 contains components which are reflected at the face 10a at various angles.

The photodetector 16 in the form a line sensor comprising an array of photosensors is positioned so that the array of photosensors extends in the direction in which the reflecting angle varies.

Analysis of a sample by the surface plasmon sensor of this embodiment will be described, hereinbelow.

That is, the sample 11 is placed on the sample support side of the metal film 12. When effecting analysis, a light beam 13 converged in the manner described above is caused to impinge upon the face 10a of the prism 10. The light beam 13 reflected in total reflection from the face 10a is detected by the photodetector 16.

When the light beam 13 is reflected in total reflection at the face 10a, evanescent waves ooze out from the face 10a toward the metal film 12. When the light beam 13 impinges upon the face 10a at a particular angle of incidence θsp, the evanescent waves excite surface plasmon on the surface of the metal film 12, and the intensity I of the light reflected from the face 10a at an angle corresponding to the angle θsp greatly drops.

Accordingly, by checking the amounts of light received by the respective photosensors of the photodetector 16 on the basis of the light amount signal S1, and detecting the angle of incidence θsp at which the intensity I of the light reflected from the face 10a greatly drops, a specific material in the sample 11 can be quantitatively analyzed according to a standard curve showing the relation between the angle of incidence θ of the light beam to the face 10a and the intensity I of the reflected light which has been determined for each sample.

As described above, in order to effect accurate measurement by use of the Otto type surface plasmon sensor, it is necessary to keep constant the distance between the face 10a of the prism 10 and the sample support side of the metal film 12 within the range by which the evanescent waves ooze out from the face 10a of the prism 10. In this embodiment, this requirement is met in the following manner.

When the distance measuring light beam 20 is caused to enter the prism 10 and impinge upon the face 10a of the prism 10 so as to be reflected in total reflection at the face 10a, evanescent waves ooze out from the face 10a. When the distance between the face 10a of the prism 10 and the metal film 12 is within the distance which the evanescent waves can reach, the evanescent waves are absorbed by the metal film 12.

Accordingly the amount of distance measuring light beam 20 reflected at the face 10a is reduced. The reduction in the amount of distance measuring light beam 20 reflected at the face 10a solely depends upon the distance between the face 10a and the sample support side of the metal film 12. On the basis of this fact, the light amount signal S2 representing the amount of the distance measuring light beam 20 reflected in total reflection at the dace 10a is input into the data processing section 26 and the data processing section 26 inputs a drive control signal S3 into the driver 23 to control the piezo-electric element 22 so that the light amount signal S2 is kept constant, whereby the distance between the face 10a of the prism 10 and the sample support side of the metal film 12 can be kept constant.

Figure 3:
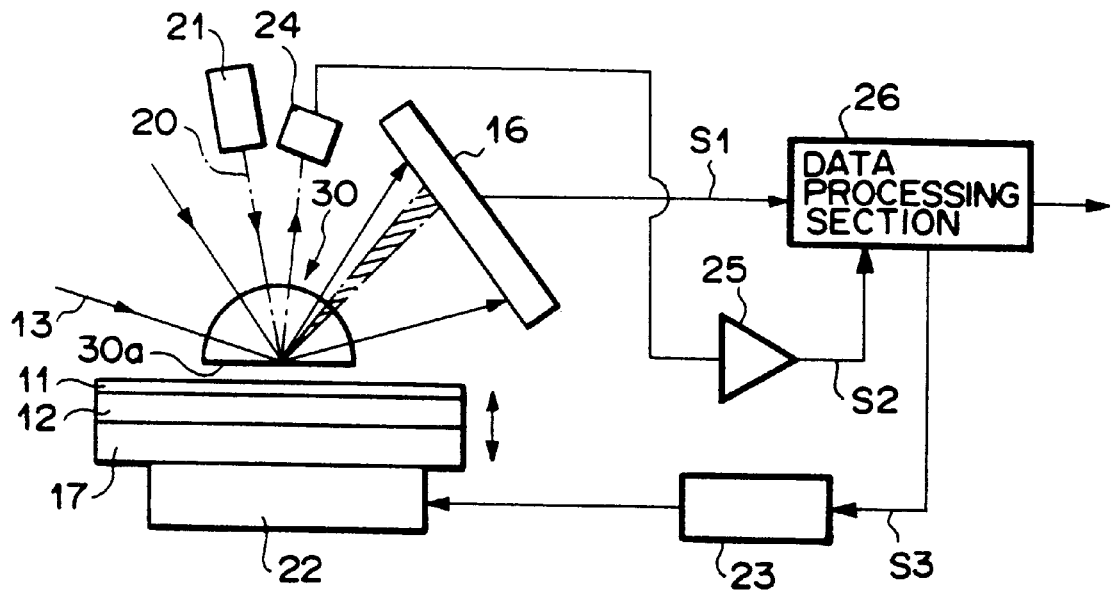
FIG. 3 is a side view of a surface plasmon sensor in accordance with a second embodiment of the present invention.
Figure 4:
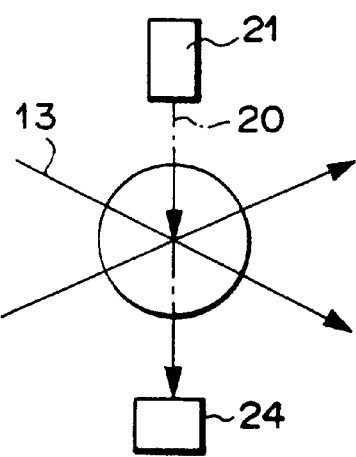
FIG. 4 is a fragmentary plan view showing a part of the surface plasmon sensor of the second embodiment.

A second embodiment of the present invention will be described with reference to FIGS. 3 and 4, hereinbelow. In FIGS. 3 and 4, the elements analogous to those shown in FIGS. 1 and 2 are given the same reference numerals and will not be described here.

The surface plasmon sensor of the second embodiment differs from that of the first embodiment in that a semi-cylindrical prism 30 is employed in place of the triangular prism 10. Further, as clearly shown in FIG. 4, in the second embodiment, the distance measuring light source 21 is disposed so that the optical path of the distance measuring light beam 20 is substantially at 900 to that of the light beam 13 as seen in plan, which facilitates layout of the distance measuring light source 21 and the photodetector 24.

In this embodiment, the distance between the face 30a of the prism 30 and the metal film 12 is kept constant in the manner similar to that in the first embodiment.

Figure 5:
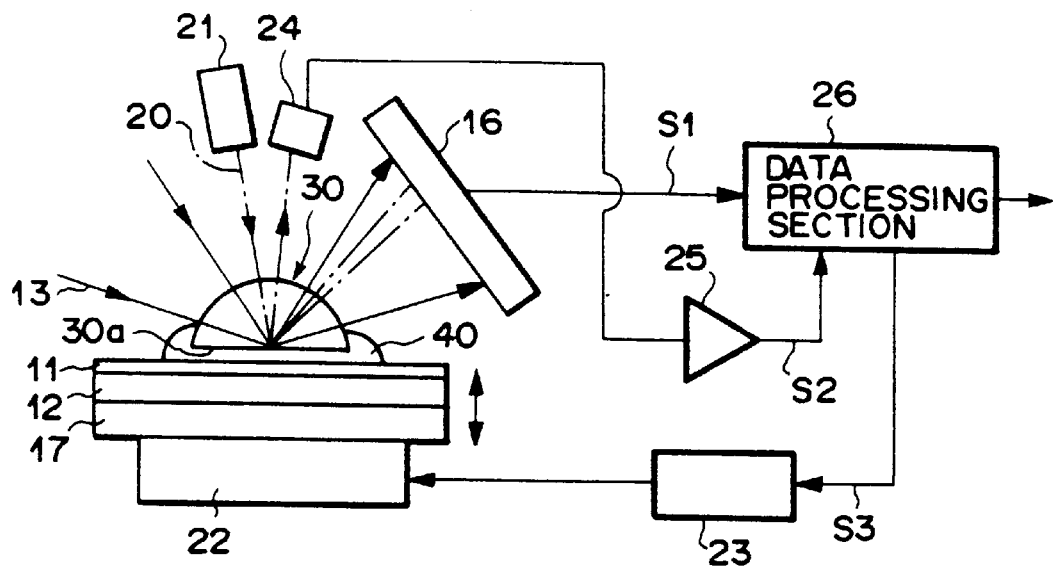
FIG. 5 is a side view of a surface plasmon sensor in accordance with a third embodiment of the present invention.

A third embodiment of the present invention will be described with reference to FIG. 5, hereinbelow.

The surface plasmon sensor of the third embodiment differs from that of the second embodiment in that liquid 40 is disposed between the prism 30 and the sample 11 and the sample 11 is analyzed in the liquid 40. In this case, the refractive index $n_s$ of the prism 30 should be larger than the refractive index $n_L$ of the liquid 40.

In this embodiment, the distance between the face 30a of the prism 30 and the metal film 12 is kept constant in the manner similar to that in the first embodiment.

Figure 6:
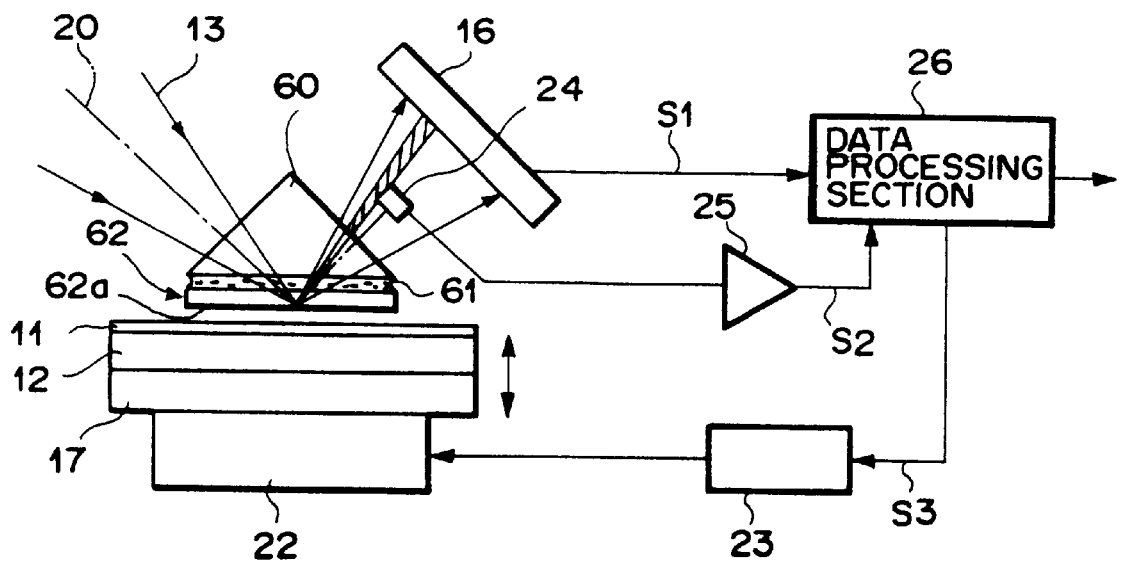
FIG. 6 is a side view of a surface plasmon sensor in accordance with a fourth embodiment of the present invention.

A fourth embodiment of the present invention will be described with reference to FIG. 6, hereinbelow.

The surface plasmon sensor of the fourth embodiment differs from that of the first embodiment in that a substantially rectangular dielectric block 62 is used in place of the prism 10. The dielectric block 62 is connected to the lower surface of a prism 60 with a refractive index matching fluid 61 intervening therebetween.

In this plasmon sensor, the distance measuring light beam 20 is caused to enter the prism 60 to be reflected in total reflection at a lower face 62a of the block 62. The block 62 and the prism 60 are formed of the same material. Since the block 62 and the prism 60 are formed of the same material and are connected by way of the refractive index matching fluid 61 which is equal to the block 62 and the prism 60 in refractive index, they form a system which is optically equivalent to an integral prism.

In this embodiment, the distance between the face 62a of the block 60 and the metal film 12 is kept constant in the manner similar to that in the first embodiment.

What is claimed is:

1. A surface plasmon sensor comprising
   a dielectric block,
   a metal film having a sample supporting side which is faced toward one face of the dielectric block spaced therefrom and on which a sample is placed,
   a light source emitting a light beam,
   an optical system which causes the light beam to enter the dielectric block so that the light beam is reflected in total reflection at said one face of the dielectric block and various angles of incidence of the light beam to said one face of the dielectric block including an angle of incidence at which surface plasmon is generated can be obtained, and
   a detecting means which detects the angle of incidence of the light beam at which attenuation in total reflection takes place and the amount of reflected light is reduced,
   wherein the improvement comprises
   a distance measuring light source which causes a distance measuring light beam, at a wavelength which can be absorbed by the metal film, to enter the dielectric block so that the distance measuring light beam is reflected in total reflection at said one face of the dielectric block,
   a drive means which moves the dielectric block and the metal film relatively to each other so that the distance between said one face of the dielectric block and the sample support side of the metal film changes,
   a photodetector which measures the amount of distance measuring light beam reflected in total reflection at said one face of the dielectric block, and
   a control means which controls the drive means to move the dielectric block and the metal film so that the amount of reflected distance measuring light beam as detected by the photodetector is kept constant.

2. A surface plasmon sensor se defined in claim 1 in which the dielectric block is shaped like a prism.

3. A surface plasmon sensor as defined in claim 1 in which the dielectric block is integrated with a prism with a refractive index matching fluid intervening therebetween, the dielectric block, the prism and the refractive index matching fluid being equal to each other in refractive index, and said light beams are caused to enter the prism to be reflected in total reflection at a face of the dielectric block.

* * * * *